United States Patent [19]

Steer et al.

[11] 4,133,904
[45] Jan. 9, 1979

[54] TREATMENT OF SINGLE CELL PROTEIN

[75] Inventors: David C. Steer; Hugh L. Williams, both of Norton, England

[73] Assignee: Imperial Chemical Industries Limited, London, England

[21] Appl. No.: 704,673

[22] Filed: Jul. 12, 1976

[30] Foreign Application Priority Data

Jul. 16, 1975 [GB] United Kingdom ............... 29841/75

[51] Int. Cl.² .............................................. A23J 1/00
[52] U.S. Cl. .................................... 426/656; 426/62; 260/112 R
[58] Field of Search ...................... 426/60, 61, 62, 656; 195/2, 4, 5, 28 R, 96; 260/112 R

[56] References Cited

U.S. PATENT DOCUMENTS

| | | | |
|---|---|---|---|
| 3,784,536 | 1/1974 | Akin et al. | 260/112 R |
| 3,809,776 | 5/1974 | Chao | 426/60 X |
| 3,878,093 | 4/1975 | Kanani et al. | 195/28 R X |
| 3,947,605 | 3/1976 | Chao | 426/60 X |

Primary Examiner—R. B. Penland
Attorney, Agent, or Firm—Cushman, Darby & Cushman

[57] ABSTRACT

A process for treating single cell protein particularly of bacterial origin in order to reduce the nucleic acid content thereof and thereby render it more suitable for human consumption. The process involves subjecting a culture containing microorganism cells to three main steps namely, (A) treatment with acid to lower pH, (B) heating and (C) treatment with alkali to raise pH. The microorganism cells are thereafter removed from the culture medium.

11 Claims, No Drawings

TREATMENT OF SINGLE CELL PROTEIN

This invention relates to a process for the treatment of single cell protein to reduce the nucleic acid content thereof.

Single cell protein which may be obtained by the cultivation of microorganisms in continuous fermentation generally contains a higher proportion of nucleic acids than is contained in the majority of other foods and feedstuffs. For some potential applications of single cell protein there may be a benefit in reducing this high nucleic acid level to some extent.

For instance if the single cell protein is intended for human consumption a reduction in its nucleic acid content is to be preferred. Human beings lack the enzyme uricase and, unlike animals which possess this enzyme, are unable to convert uric acid derived from nucleic acids to allantoin. Thus in human foods a high level of nucleic acids is undesirable.

Methods proposed for the removal of nucleic acids from single cell protein frequently involve the mechanical disruption of the cells. This operation enables the nucleic acids from the cells to be dissolved out, advantage being taken of the different solubility properties of nucleic acids compared with protein. For example in "The Nucleic Acids", Volume 1, Edited by E. Chargaff and J. N. Davidson, Academic Press 1955, at page 391, a method is described for the separation and recovery of ribonucleic acid (which normally accounts for the greater part of the nucleic acids in single cell protein) which involves fragmentation of the cells using a wet crushing mill, followed by extraction with hot salt solutions. Hot salt solutions have the advantage of minimizing protein solubility, whilst being good solvents for nucleic acids.

In our UK Specification No. 1 381 306 we describe and claim a method for separating bacterial cells from an aqueous medium wherein the cells are flocculated by subjecting the medium to at least one of the steps of:

(A) raising the pH of the medium to a value within the range 8 to 11 by treatment with an alkali, and (B) heating the medium to a temperature within the range 50° to 200° C; step (A) and/or step (B) being followed by the further step of lowering the pH to a value within the range 2 to 5 by treatment with an acid, and the flocculated cells are separated from the medium.

We have now found that the method of UK Specification No. 1 381 306 may be adapted to give a process whereby single cell protein having a reduced nucleic acid content may be produced.

According to the present invention we provide a process for the treatment of single cell protein wherein an aqueous medium containing microorganism cells is subjected to the steps of (A) treatment with an acid to lower its pH to a value not greater than 5 and (B) heating to a temperature of at least 60° C, steps (A) and (B) being performed in either order or at the same time, and subsequently (C) treatment with an alkali to raise the pH of the medium to a value of at least 6 whilst maintaining the temperature of the medium at a value of at least 60° C and thereafter the cells are separated from the medium.

By the process of the invention the nucleic acid content of the microorganism cells constituting the single cell protein is reduced without recourse to mechanical fragmentation of the cells which is undesirable. We believe that this desirable result is achieved for the following reason. The heat and acid treatment followed by alkali treatment render the cells permeable to nucleic acids possibly by removing parts of the outer layers of the cell walls. The nucleic acids permeate through the weakened cell walls into the surrounding medium and the nucleic acid content of the cells is thereby reduced. When the cells are separated from the medium they are separated from the nucleic acids therein.

The microorganism cells which constitute the single cell protein can be yeast cells or bacterial cells, preferably the latter. The process is very suitable for treating bacterial cells of the genera Pseudomonas, Alcaligenes and Bacillus, for example strains of the species *Pseudomonas fluorescens*, *Pseudomonas aeroginosa*, *Pseudomonas diminuta*, *Alcaligenes faecalis*, *Bacillus cereus* and particularly *Pseudomonas methylotropha*. This last is a species whose characteristics are described in our UK Specification No. 1 370 892. Cultures of a number of strains of this last species have been deposited in and are available from the National Collection of Industrial Bacteria (NCIB), Torry Research Station, Aberdeen, Scotland, UK and corresponding deposits have been made in the collections of the US Department of Agriculture (NRRL) at Peoria, Illinois and the Fermentation Research Institute (FRI) in Japan. The numerical designations given to these cultures are as follows:

NCIB Nos. 10508-15 and 10592-6
NRRL Nos. B 5352-64
FRI Nos. FERM 1215 - 27

Other bacterial species which may be treated by the process are *Pseudomonas rosea*, *Microcylus polymorphum* and *Hyphomicrobium variabile*. The characteristics of these species also are given in our UK Specification No. 1 370 892 and cultures of a number of strains have been deposited at the above depositories and are available from NCIB. The numerical designations of these last cultures are as follows:

NCIB Nos. 10516-7 and 10597-612
NRRL Nos. B 5381-2 and B 5365-80
FRI Nos. FERM 1228-45

In carrying out the process of the present invention the alkali treatment step (in which the pH of the medium is raised to a value within the range 8 to 11 by treatment with an alkali) of the method of our UK Specification No. 1 381 306 may be performed before heating and treating with acid without any disadvantage.

During heating of the medium (step B) the temperature is suitably raised to 60° to 100° C, preferably 70° to 90° C. The acid treatment (step A) suitably lowers the pH to a value within the range 2 to 5, preferably 2.5 to 4.5. The subsequent treatment with an alkali (step C) suitably raises the pH to a value within the range 6 to 10, preferably 6 to 8. Before treatment with alkali (step C) the medium is preferably both heated and maintained at the lower pH suitably for a period of at least one minute, preferably two to ten minutes.

After maintaining the medium at an elevated temperature and lowered pH for a period the temperature should be maintained at at least 60° C during the alkali treatment. It is advantageous to remove some of the medium before treating with alkali to reduce the cost of treatment.

The acid used to treat the medium may suitably be an inorganic acid such as sulphuric, hydrochloric or phosphoric acid or an acid gas such as carbon dioxide or sulphur dioxide. When the process forms a step in an overall process for single cell protein production the acid is preferably a phosphoric/sulphuric acid mixture of suitable proportions to enable the medium, after separation of flocculated cells, to be recirculated to the fermentation stage of the process. After acidification and heating it is preferred that treatment with alkali should be as mild as possible to minimize the break up of the large flocs formed during the acidification and heating treatment. Suitable alkalis include sodium hydroxide, calcium hydroxide, sodium carbonate and ammonia.

For treatment by the process of the invention the medium preferably contains 0.05 to 2% w/v of a salt, suitably sodium chloride or ammonium phosphate.

Following treatment with alkali, separation of flocculated cells may be effected by conventional techniques such as centrifugation or filtration or by flotation.

The invention is illustrated by the following Example:

EXAMPLE 1

A ten per cent suspension of flocculated cells of an organism of the species *Pseudomonas methylotropha*, formed as described in our UK Specification No. 1 381 306 was thereafter treated as follows:

Fifty grammes of sodium chloride were added to five liters of medium and the pH was raised from 4.3 to 7.0 using dilute caustic soda solution. The temperature was raised to 80° C and maintained for five minutes. The treated medium was mixed with thirty five liters of hot water and the SCP was recovered by centrifugation. The SCP was dried in a vacuum oven at 50° C.

The analysis of the treated sample is shown in Table 1 in which the results are compared with those given by a similar sample of flocculated cells, which had not been treated to reduce the nucleic acid. From the table it can be seen that the nucleic acid content of the treated sample is much lower.

TABLE 1

| Analysis | Treated Sample | Untreated Sample |
| --- | --- | --- |
| Loss at 105° C | 2.9% | 4.4% |
| Ash at 550° C | 3.1% | 8.3% |
| Total P | 0.8% | 2.6% |
| Total S | 0.2% | 0.99% |
| Total Cl | 0.64% | <0.02% |
| Total Ca | 0.18% | 0.12% |
| Total Na | 0.38% | 1.13% |
| Total K | 0.02% | 0.22% |
| Ammonia $N_2$ | 0.006% | 0.05% |
| Total $N_2$ | 13.4% | 13.0% |
| Nucleic acid | 1.8% | 14.7% |
| Total acid | 6.8% | 5.9% |
| Total anhydro amino acids | 69.9% | 57.3% |
| Aspartic acid | 8.3% | 7.2% |
| Threonine | 4.3% | 3.7% |
| Serine | 3.2% | 2.7% |
| Glutamic acid | 10.2% | 8.4% |
| Proline | 3.3% | 2.7% |
| Glycine | 4.9% | 4.2% |
| Alanine | 6.6% | 5.6% |
| Valine | 5.7% | 4.5% |
| Methonine | 2.6% | 2.0% |
| Isoleucine | 4.7% | 3.8% |
| Leucine | 7.5% | 5.8% |
| Tyrosine | 3.1% | 2.6% |
| Phenylalanine | 3.7% | 2.9% |
| Histidine | 1.9% | 1.6% |
| Lysine | 6.4% | 5.4% |
| Arginine | 5.1% | 4.0% |

Table — The analysis of samples of *Pseudomonas methylotropha* with and without treatment to reduce the nucleic acid.

EXAMPLE 2

Seven cultures each of one of the strains *Pseudomonas methylotropha* ASI (NCIB 10515), *Pseudomonas diminuta, Pseudomonas aeroginosa, Pseudomonas fluorescens, Pseudomonas alcaligenes, Alcaligenes faecalis,* and *Bacillus cereus* were grown up in shake flasks to give 1 l of culture. Each culture was divided into two parts and one part was diluted with an equal volume of water, centrifuged and dried in a vacuum oven at 50° C. This part formed the control. The other part was heated to 80° C with 1% w/v Na Cl added. The pH was then lowered to 4 for 10 minutes and thereafter the culture was reneutralised for 5 minutes, diluted 2 times volume, centrifuged and dried in a vacuum oven at 50° C. Nucleic acid determinations were made. The results are set out in Table 2.

TABLE 2

| Strain | Nucleic acid content of control (% $^w/_v$) | Nucleic acid content of test culture (% $^w/_w$) |
| --- | --- | --- |
| P. methylotropha AS-1 | 10.1 | 3.5 |
| P. diminuta | 9.2 | 3.9 |
| P. aeroginosa | 7.1 | 7.0 |
| P. fluorescens | 11.7 | 4.7 |
| P. alcaligenes | 11.6 | 4.9 |
| Alcaligenes faecalis | 10.3 | 6.2 |
| Bacillus cereus | 4.5 | 2.2 |

EXAMPLE 3

Two cultures, one each of a Ps. fluorescens and a Ps. alcaligenes strain, were treated as in Example 2 with the exception that the addition of Na Cl was omitted. The Results were as follows:

| | Nucleic acid content of control (% $^w/_v$) | Nucleic acid content of test culture (% $^w/_w$) |
| --- | --- | --- |
| Ps. fluorescens | 10.9 | 7.0 |
| Ps. Alcaligenes | 9.3 | 4.8 |

We claim:

1. A process for the treatment of single cell protein consisting essentially of:

(A) treating an aqueous medium containing microorganism cells with an acid to lower its pH to a value not greater than 5, (B) heating said aqueous medium containing microorganism cells for a period of from two to ten minutes to a temperature of at least 60° C, steps (A) and (B) being performed in either order or at the same time, and subsequently (C) treating said aqueous medium containing microorganism cells with an alkali to raise pH of the medium to a value of at least 6 whilst maintaining the temperature of the medium at a value of at least 60°, and (D) separating the cells from the aqueous medium.

2. A process according to claim 1 wherein the cells are cells of a genus selected from the group consisting of Pseudomonas, Alcaligenes and Bacillus.

3. A process according to claim 2 wherein the cells are cells of the species *Pseudomonas methylotropha*.

4. A process according to claim 1 wherein, before step (A) and/or step (B), the pH of the medium is raised to a value within the range 8 to 11 by treatment with an alkali.

5. A process according to claim 1 wherein during step (B) the temperature of the medium is raised to a value within the range 60° to 100° C.

6. A process according to claim 1 wherein during step (A) the pH of the medium is lowered to a value within the range 2 to 5.

7. A process according to claim 1 wherein during step (C) the pH of the medium is raised to a value within the range 6 to 10.

8. A process according to claim 1 wherein the acid used in step (A) is an acid selected from the group consisting of sulphuric acid, hydrochloric acid and phosphoric acid.

9. A process according to claim 1 wherein the alkali used in step (C) is an alkali selected from the group consisting of sodium hydroxide, calcium hydroxide, sodium carbonate and ammonia.

10. A process according to claim 1 wherein the medium contains 0.05% to 2% w/v of a salt.

11. A process for the treatment of single cell protein consisting of:
(A) treating an aqueous medium containing nicroorganism cells with an acid to lower its pH to a value not greater than 5,
(B) heating said aqueous medium containing microorganism cells for a period of from two to ten minutes to a temperature of at least 60° C, steps (A) and (B) being performed in either order or at the same time, and subsequently
(C) treating said aqueous medium containing microorganism cells with an alkali to raise pH of the medium to a value of at least 6 whilst maintaining the temperature of the medium at a value of at least 60° C, and
(D) separating the cells from the aqueous medium.

* * * * *